United States Patent
Kumar et al.

(10) Patent No.: US 6,602,999 B1
(45) Date of Patent: Aug. 5, 2003

(54) AMORPHOUS FORM OF CEFPODOXIME PROXETIL

(75) Inventors: Yatendra Kumar, Haryana (IN); Rakesh Kumar Arora, Haryana (IN); Kaptan Singh, Uttar Pradesh (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/048,354

(22) PCT Filed: Jul. 24, 2000

(86) PCT No.: PCT/IB00/01024
§ 371 (c)(1),
(2), (4) Date: May 21, 2002

(87) PCT Pub. No.: WO01/09143
PCT Pub. Date: Feb. 8, 2001

(30) Foreign Application Priority Data

Jul. 30, 1999 (IN) .................................. 1036/DEL/1999

(51) Int. Cl.$^7$ ............................................. C07D 501/34
(52) U.S. Cl. ....................................... 540/220; 540/228
(58) Field of Search ................................. 540/228, 220

(56) References Cited

U.S. PATENT DOCUMENTS

| 4,486,425 A | 12/1984 | Nakao et al. ................ 424/246 |
| 4,562,181 A | 12/1985 | Crisp et al. .................. 514/202 |
| 5,248,699 A | 9/1993 | Sysko et al. ................. 514/647 |
| 6,107,290 A | 8/2000 | Woo et al. ................... 514/200 |

FOREIGN PATENT DOCUMENTS

| EP | 0 014 590 A1 | 8/1980 |
| EP | 0 022 527 B1 | 4/1983 |
| EP | 0 490 648 B1 | 12/1995 |

OTHER PUBLICATIONS

Konne, T., *Chem. Pharm. Bull.*, 38, 2003 (1990).

*Primary Examiner*—Mark L. Berch
(74) *Attorney, Agent, or Firm*—Jayadeep R. Deshmukh, Esq.

(57) ABSTRACT

A novel process for the production of an improved amorphous form of cefpodoxime proxetil [(6R-[6α,7β(Z))]-7-{E (2-Amino-4-thiazolyl)(methoxyimino)acetyl]amino]-3-(methoxymethyl)-8-oxo-5-thia-1-azabicyclo[4.2.0]oct-2-ene-2-carboxylic acid-1-[[(1-methylethoxy)carboxylic acid-1-[[(1-methylethoxy)carbonyl]oxy]ethyl ester, is described.

8 Claims, 2 Drawing Sheets

AMORPHOUS FORM OF CEFPODOXIME PROXETIL

FIELD OF THE INVENTION

This invention relates to an improved amorphous form of cefpodoxime proxetil and a novel process for the production thereof.

BACKGROUND OF THE INVENTION

Chemically, cefpodoxime proxetil is [(6R-[6α,7β(Z))]-7-{E(2-Amino-4-thiazolyl)(methoxyimino)acetyl]amino]-3-(methoxymethyl)-8-oxo-5-thia-1-aza-bicyclo[4.2.0]oct-2-ene-2-carboxylic acid-1-[[(1-methylethoxy)carboxylic acid-1-[[(1-methylethoxy)carbonyl]oxy]ethyl ester having the following formula

FORMULA I

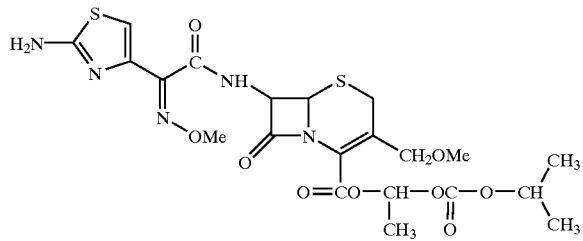

and is covered in U.S. Pat. No. 4,486,425. Cefpodoxime Proxetil is a valuable antibiotic characterized by high broad spectrum activity against gram-positive and gram-negative micro-organisms. It has also been found to be highly active against susceptible and resistant strains of N. gonorrheae.

The latest trend in the pharmaceutical industry is to study polymorphism in drugs as well as the difference in the activity of different polymorphic forms of a given drug. The term polymorphism includes different physical forms, crystal forms, crystalline/liquid crystalline/non-crystalline (amorphous) forms. This has become very interesting especially after observing that many antibiotics, antibacterials, tranquilizers etc., exhibit polymorphism and one or more of the polymorphic forms of a given drug exhibit superior bio-availability and consequently show much higher activity compared to other polymorphs. It has also been disclosed that the amorphous forms in a number of drugs exhibit different dissolution characteristics and in some cases different bioavailability patterns compared to the crystalline form [Konne T., Chem. Pharm. Bull., 38, 2003 (1990)]. For some therapeutic indications one bioavailability pattern may be favored over another. Sertraline, Frenitizole, Sulphathiazole, Indomethacine etc. are some of the important examples of pharmaceuticals which exhibit polymorphism. A host of patents have been granted pertaining to these drugs. To cite a few, U.S. Pat. No. 5,248,699 discusses about five polymorphic forms of sertraline hydrochloride while EP 014590 describes four polymorphic forms of Frentizole. EP 490648 and EP 022527 also deal with the subject of polymorphism in drugs.

Since cefpodoxime proxetil is poorly absorbed from the gastrointestinal tract, it is therefore present in sera and urine only in low concentrations after oral administration. Accordingly, there has been a need for a form of cefpodoxime proxetil which has better intrinsic dissolution and is capable of being better absorbed from the gastrointestinal tract following oral administration.

SUMMARY OF THE INVENTION

In accordance with the first aspect of the present invention, an efficient method is provided for the preparation of an amorphous form of cefpodoxime proxetil which has better intrinsic dissolution when compared with that of cefpodoxime proxetil prepared by conventional solvent precipitation.

The second aspect of the present invention provides a process for the preparation of cefpodoxime proxetil in an amorphous form which comprises dissolving cefpodoxime proxetil prepared by the conventional solvent precipitation in a suitable solvent followed by recovering amorphous form of cefpodoxime proxetil from the solution thereof by spray drying, wherein the amorphous form has a better intrinsic dissolution rate than cefpodoxime proxetil prepared by conventional solvent precipitation.

The term "suitable solvent" is selected from the group consisting of ketones, alcohols, esters, chlorinated solvents, ethers, acetonitrile and mixtures thereof. Preferably, the solvent is selected from the group consisting of acetone, methanol, ethanol ethylacetate, chloroform, dichloromethane, tetrahydrofuran, 1,4-dioxan and mixtures thereof.

In accordance with the present invention cefpodoxime proxetil is recovered from the solution in an amorphous form using a spray drying technique. The Mini-Spray-Dryer (Model: Buchi 190, Switzerland) which is used, operates on the principle of nozzle spraying in parallel-flow i.e. the sprayed product and the drying gas flow in the same direction. The drying gas can be air or inert gases such as nitrogen, argon, and carbon dioxide. Nitrogen is preferred in this case.

OBJECTS OF THE INVENTION

The first object of the invention is to prepare a pharmaceutical composition comprising cefpodoxime proxetil in an amorphous form that has a better intrinsic dissolution rate than that of cefpodoxime proxetil prepared by the chemical method alone.

The second object of the invention is to develop a process for the preparation of cefpodoxime proxetil in an amorphous form which comprises dissolving cefpodoxime proxetil prepared by the conventional solvent precipitation method in a suitable solvent and recovering an amorphous form of cefpodoxime proxetil from said solution by a spray drying technique wherein the amorphous form has a better intrinsic dissolution rate than that of cefpodoxime proxetil prepared by the conventional solvent precipitation method alone.

DETAILED DESCRIPTION OF THE INVENTION

The present invention is illustrated by the following examples which are not intended to limit the effective scope of the claims:

EXAMPLE 1

Cefpodoxime Proxetil (100 gm) was dissolved in acetone (770 ml) at 25–30° C. The clear solution so obtained was subjected to spray drying in a mini-spray dryer (Buchi model 190) at an inlet temperature of 75° C. and outlet temperature of 55° C. with a feed rate of 15 ml per minute. Cefpodoxime proxetil (80 gm) in an amorphous form was thus isolated.

Figure 1:
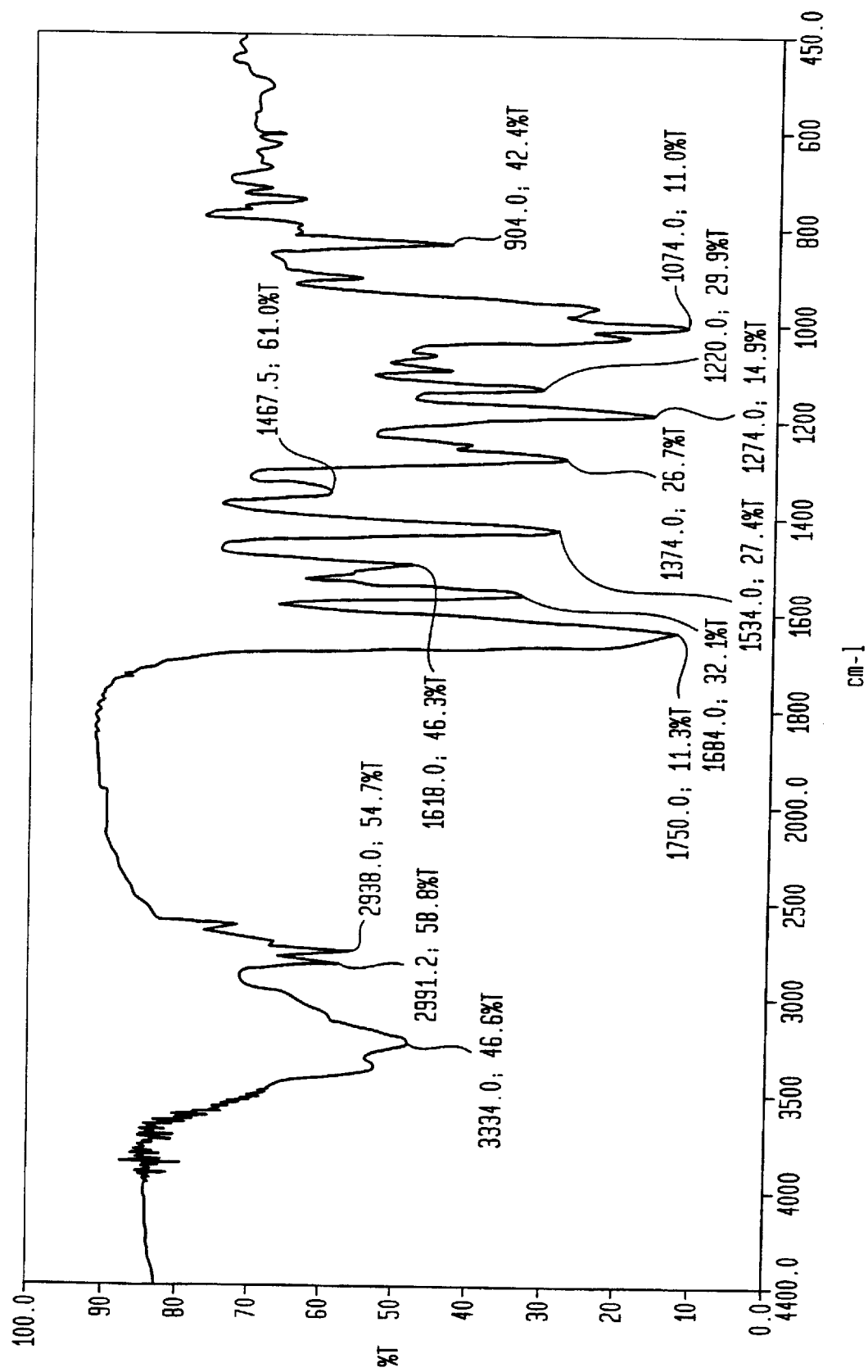
FIG. 1 shows the infra-red spectrum of the amorphous cefpodoxime proxetil prepared according to the process of the present invention.
Figure 2:
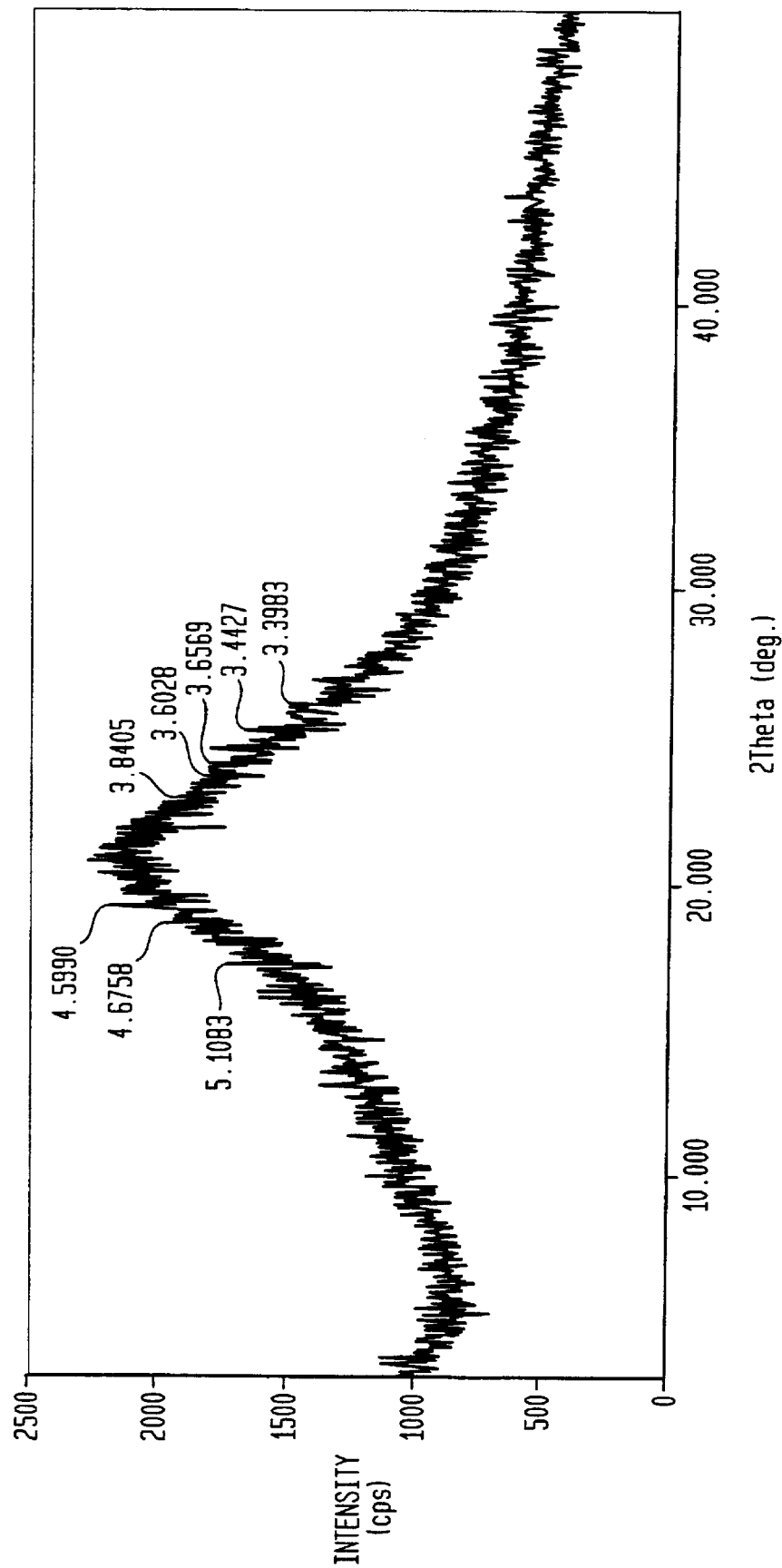
FIG. 2 shows the X-ray powder diffraction pattern which demonstrates the amorphous nature of the cefpodoxime proxetil prepared according to the present invention.

Infrared spectrum in KBr (FIG. 1), and X-ray powder diffraction pattern (FIG. 2), as shown in the accompanying drawings, confirmed the amorphous nature of the product.

EXAMPLE 2

Cefpodoxime Proxetil (100 gm) was dissolved in methanol (600 ml) at 25–30° C. The clear solution so obtained was subjected to spray drying in a mini-spray dryer (Buchi Model 190) at an inlet temperature of 75° C. and outlet temperature of 58° C. with a feed rate of 15 ml per minute. Cefpodoxime proxetil (83 gm) in an amorphous form was thus isolated.

Infrared spectrum in KBr and X-ray diffraction pattern confirmed the amorphous nature of the product.

While the present invention has been described in terms of its specific embodiments, certain modifications and equivalents will be apparent to those skilled in the art and are intended to be included within the scope of the present invention.

What is claimed is:

1. Cefpodoxime proxetil in an amorphous form which is prepared by a process that comprises preparing a solution of cefpodoxime proxetil in a suitable solvent and recovering an amorphous form of cefpodoxime proxetil from the solution by spray drying.

2. The process of claim 1 wherein the suitable solvent is selected from the group consisting of ketones, alcohols, esters, chlorinated solvents, ethers, acetonitrile and mixtures thereof.

3. The process of claim 2 wherein the solvent is selected from the group consisting of acetone, methanol, ethanol, ethylacetate, chloroform, dichloromethane, tetrahydrofuran, 1,4-dioxane and mixtures thereof.

4. The process of claim 3 wherein the solvent is selected from the group consisting of acetone, methanol or ethanol and mixtures thereof.

5. A process for the preparation of amorphous cefpodoxime proxetil that comprises preparing a solution of cefpodoxime proxetil in a suitable solvent and recovering amorphous form of cefpodoxime proxetil from said solution by spray drying.

6. The process of claim 5 wherein the suitable solvent is selected from the group consisting of ketones, alcohols, esters, chlorinated solvents, ethers, acetonitrile and mixtures thereof.

7. The process of claim 6 wherein the solvent is selected from the group consisting of acetone, methanol, ethanol, ethylacetate, chloroform, dichloromethane, tetrahydrofuran, 1,4-dioxane and mixtures thereof.

8. The process of claim 7 wherein the solvent is selected from the group consisting of acetone, methanol or ethanol and mixtures thereof.

* * * * *